(12) United States Patent
Hughes et al.

(10) Patent No.: US 7,858,953 B2
(45) Date of Patent: Dec. 28, 2010

(54) USE OF FLUORESCENT NANOPARTICLES TO MEASURE INDIVIDUAL LAYER THICKNESSES OR COMPOSITION IN MULTI-LAYER FILMS AND TO CALIBRATE SECONDARY MEASUREMENT DEVICES

(75) Inventors: Michael Kon Yew Hughes, Vancouver (CA); Sebastien Tixier, North Vancouver (CA)

(73) Assignee: Honeywell ASCa Inc., Mississauga (CA)

( * ) Notice: Subject to any disclaimer, the term of this patent is extended or adjusted under 35 U.S.C. 154(b) by 22 days.

(21) Appl. No.: 12/125,932

(22) Filed: May 23, 2008

(65) Prior Publication Data
US 2009/0289199 A1  Nov. 26, 2009

(51) Int. Cl.
*G01N 21/64* (2006.01)
(52) U.S. Cl. .................................... 250/459.1
(58) Field of Classification Search ............... 250/459.1
See application file for complete search history.

(56) References Cited

U.S. PATENT DOCUMENTS

| | | | |
|---|---|---|---|
| 4,239,593 A | 12/1980 | Dunsmoor, Jr. | |
| 4,311,658 A | 1/1982 | Nicoll | |
| 4,376,012 A | 3/1983 | Bergstrom | |
| 4,577,337 A | 3/1986 | Light | |
| 4,767,935 A * | 8/1988 | Anderson et al. | 250/559.04 |
| 4,783,314 A | 11/1988 | Hoots et al. | |
| 4,797,246 A | 1/1989 | Reinke et al. | |
| 4,879,471 A | 11/1989 | Dahlquist | |
| 4,908,278 A * | 3/1990 | Bland et al. | 428/500 |
| 4,943,721 A | 7/1990 | Vidrine, Jr. | |
| 5,094,535 A | 3/1992 | Dahlquist et al. | |
| 5,230,923 A | 7/1993 | Hirokawa et al. | |
| 5,315,124 A | 5/1994 | Goss et al. | |
| 5,432,353 A | 7/1995 | Goss et al. | |
| 5,455,422 A * | 10/1995 | Anderson et al. | 250/341.1 |
| 5,795,394 A | 8/1998 | Belotserkovsky et al. | |
| 5,854,821 A | 12/1998 | Chase et al. | |
| 5,900,113 A | 5/1999 | Tubergen | |
| 6,074,483 A | 6/2000 | Belotserkovsky et al. | |
| 6,086,716 A | 7/2000 | Watson et al. | |
| 6,092,003 A | 7/2000 | Hagart-Alexander et al. | |

(Continued)

OTHER PUBLICATIONS

Hidrovo et al., "Excitation nonlinearities in emission reabsorption laser-induced fluorescence techniques," 2004, Applied Optics, vol. 43, No. 4 pp. 894-913.*

(Continued)

*Primary Examiner*—David P Porta
*Assistant Examiner*—Kiho Kim
(74) *Attorney, Agent, or Firm*—Cascio Schmoyer & Zervas

(57) ABSTRACT

Fluorescent nanoparticles such as quantum dots are incorporated into plastic, paper and other web layered products to achieve cross-direction and machine direction on-line analysis of the individual layers therein. Fluorescent nanoparticles markers are added in known proportions into product formulations. By detecting the fluorescence from the nanoparticles, the thickness and other physical characteristics of the web can be traced at various stages of production. In addition, by using different populations of fluorescent nanoparticles that emit radiation at different wavelengths, data from individual layers in a composite structure can be ascertained simultaneously with a single sensor. The technique is particularly suited for monitoring difficult-to-measure polymers in complex multi-layer structures.

21 Claims, 2 Drawing Sheets

U.S. PATENT DOCUMENTS

| | | |
|---|---|---|
| 6,410,926 B1 | 6/2002 | Munro et al. |
| 6,466,839 B1 | 10/2002 | Heaven et al. |
| 6,565,343 B1 | 5/2003 | Krycki |
| 6,649,138 B2 | 11/2003 | Adams et al. |
| 6,682,810 B1 | 1/2004 | Jones et al. |
| 6,783,699 B2 | 8/2004 | Li et al. |
| 6,793,854 B1 | 9/2004 | Kirjavainen |
| 6,872,450 B2 | 3/2005 | Liu et al. |
| 6,985,221 B2 | 1/2006 | Semersky et al. |
| 7,081,489 B2 | 7/2006 | Chen et al. |
| 7,192,780 B2 | 3/2007 | Liu et al. |
| 7,255,918 B2 | 8/2007 | Watanabe et al. |
| 2006/0199023 A1* | 9/2006 | Funagi et al. ............... 428/458 |
| 2007/0119561 A1 | 5/2007 | Doelle et al. |
| 2007/0128350 A1* | 6/2007 | Nakamura et al. .......... 427/157 |
| 2007/0258316 A1 | 11/2007 | Matula |
| 2009/0032735 A1* | 2/2009 | Misawa et al. ........... 250/459.1 |

OTHER PUBLICATIONS

Hidrovo et al, "Emission reabsorption laser induced fluorescence (ERLIF) film thickness measurement," 2001, Measurement Science and Technology, vol. 12, pp. 467-477.*

Kimura et al., "Photoresist thickness measurement using laser-induced fluorescence," 1988, Applied Optics, vol. 27, No. 17., pp. 3675-3678.*

Homilius et al., "Fluorescence of plasma polymer films with embedded dye molecules," 1998, Vaccum, vol. 49, No. 3, pp. 205-211.*

Yu-Jen Shen & Yuh-Lang Lee, Assembly of CdS quantum dots onto mesoscopic TiO2 films for quantum dot-sensitized solar cell applications, Nanotechnology Jan. 4, 2008 pp. 1-7 vol. 19.

J C Grunlan et al. High-throughput measurement of polymer film thickness using optical dyes, Meas.Sci.Technol. 2005 pp. 153-161 vol. 16.

JM Corres et al. Design of pH Sensors in Long-Period Fiber Gratings Using Polymeric Nanocoatings IEEE Sensors Journal, Mar. 2007 pp. 455-463, vol. 7 No. 3.

* cited by examiner

USE OF FLUORESCENT NANOPARTICLES TO MEASURE INDIVIDUAL LAYER THICKNESSES OR COMPOSITION IN MULTI-LAYER FILMS AND TO CALIBRATE SECONDARY MEASUREMENT DEVICES

The present invention generally relates to the employment of fluorescent nanoparticles such as quantum dots to derive thickness and compositional information for one or more individual layers in a multilayer film. In particular, in the case of multilayer polymeric sheet products, known quantities of fluorescent nanoparticles are added to the individual feed stocks that form the layers to be measured. The fluorescence intensities of the layers of interest within the multilayer sheet are measured to derive the thicknesses, basis weights and other characteristics of the individual layers.

BACKGROUND OF THE INVENTION

It is known to produce multilayered structures to take advantage of different properties exhibited by the various layers in the structures. Typical of multilayered structures are multilayer films in which different layers have specific characteristics. These films may then be used in packaging applications having customized properties that may be required for a particular packaged product. For example, films which are used to protect food, medicines, paints, adhesives, biomaterials, chemicals, etc., require properties such as good thermal and environmental stability, UV blocking characteristics, transparency in visible light wavelengths and excellent moisture barrier protection.

In forming multilayer films, it is often desirable to obtain measurements of the basis weight and/or thickness of the individual layers. The "basis weight" is the mass per unit area of a material, typically measured in grams per square meter (gsm). Various sensor systems have been developed for detecting sheet properties "on-line," i.e., on a sheet-making machine while it is operating. These systems include conventional infrared (IR) absorption techniques whereby radiation of the appropriate wavelength(s) and bandwidth(s) is selected to measure the polymer(s). In the case where the film consists of two layers each formed of a different polymer, the selected radiation has at least two separate wavelength regions, one region being preferentially absorbed by polymers of the first layer and a second region being preferentially absorbed by polymers of the second layer. The thickness of each layer is proportional to the amount of radiation absorbed. As is apparent, this method is applicable when each layer is made of a different polymer; it is much less useful when one or more layers consist of polymer blends as the spectrum from each polymer typically overlaps with spectra from other polymers present in a multilayer structure. With the myriad of polymers employed in multilayer films, it is extremely difficult to find a specific region, in the radiation spectra and especially in the near infrared region, for each of the particular polymers that are substantially free from interference from other polymers. As is also apparent, the technique is not applicable where a particular polymer is present in more than one layer. Finally, conventional absorption techniques are not accurate when the layers are very thin at the gsm level.

Another system for measuring plastic films employs beta gauges that are nuclear measuring devices which emit beta rays, and which have been used to measure characteristics of single-layer plastic compositions, such as single-layer plastic films. Typically, a single-layer composition has a known beta ray absorption coefficient and a known density. Using a beta gauge, the basis weight of the single-layer plastic film can be determined. That is, by using the Beer-Lambert law, the relatively accurate, raw output of the beta gauge and the known absorption coefficient of the single-layer plastic film, the mass per unit area can be calculated for each point on the film to be measured. Similarly, the thickness of the single-layer plastic film may be calculated at each such point. The thickness of a point on the film corresponds to the mass per unit area of that point, as previously determined, divided by the known density of the plastic used to form the film. Alternatively, the mass per unit area and/or thickness of a single-layer plastic film can be measured by using a calibrated beta gauge. Calibration directly relates the beta absorption to the physical properties of the product to be measured.

Since beta gauges can only measure total film thickness, a number of beta gauges is needed to measure multilayer products. The individual layer thicknesses are obtained by measuring the total thickness of the product before and after each layer is applied. The individual thicknesses are given by subtracting the total thickness measured at the two locations. This works in principle, however the requirement of more than one scanner and sensor leads to additional costs. It is also often not possible to perform measurements before and after a layer is applied as in the case of co-extruded multilayer plastic films.

SUMMARY OF THE INVENTION

The present invention is based in part on the recognition that incorporating fluorescent nanoparticles such as quantum dots, with their unique optical emissions properties, into the individual layers of multilayer films enables on-line measurements of the individual layers during manufacture. Specifically, fluorescent nanoparticle markers or tags are mixed in known quantities with product formulations such as polymer resins that form the layers of interest. By detecting the fluorescence from the nanoparticles, the thickness, basis weight and other physical characteristics of the individual layers can be monitored at various stages of production. Moreover, by employing different populations of fluorescent nanoparticles that emit radiation at different wavelengths, data from the individual layers in a multilayer structure can be ascertained simultaneously with a single sensor.

Multilayer films typically comprise a plurality of laminated layers. Preferably, in the multilayer structure, adjacent layers are formed of different polymer materials. By employing different polymers with different physical properties, the multilayer film may have a combination of physical attributes not present in a single layer film. For example, the multilayer film may be moisture resistant, abrasion resistant, and yet remain pliable. The present invention, among other things, is effective in controlling the production of multilayer films to assure that each layer in the film has the proper thickness or weight (gsm) so that the multilayer film has the right combination of properties while minimizing the amounts of material used.

Fluorescent nanoparticles which are inorganic materials offer substantial advantages over organic dyes, including a longer half-life, a broad excitation spectrum, a narrow, symmetric emission spectrum, and minimal photo-bleaching. In particular, in multilayer films that use two or more fluorescent nanoparticle populations as markers for two or more layers, the advantages of fluorescent nanoparticles are even more evident. Specifically, each population of fluorescent nanoparticles exhibits an emission spectrum that is sufficiently narrow and selectable (e.g. by changing the nanoparticle size distribution) so that multiple colors of quantum dots can be discerned. In contrast, it is difficult to detect more than three dyes and the photo-bleaching effects make quantitative measurements less reliable and accurate. Finally, the fluorescent properties of many organic dies are temperature dependant, that is, their fluorescence is often reduced at elevated temperatures.

Accordingly, in one aspect, the invention is directed to a method of non-contact determination of a physical property of a layer of composition that includes the steps of:

(a) introducing a homogeneous distribution of fluorescent nanoparticles into the layer wherein the quantity of fluorescent nanoparticles per unit mass or volume of the layer can be determined;

(b) irradiating the layer with a light source of sufficient irradiance to create a population of excited fluorescent nanoparticles that emit fluorescent light;

(c) measuring the radiance of fluorescent light that is emitted from an area on a surface of the layer; and (d) calculating the physical property based on the measured radiance of fluorescent light.

In another aspect, the invention is directed to a method of measuring a physical property of at least two individual layers in a multilayer structure that includes the steps of:

(a) forming a multilayer structure that has at least two layers including a first layer and a second layer wherein the first layer has a homogeneous distribution of a first population of first fluorescent nanoparticle in the first layer wherein the quantity of first fluorescent nanoparticles per unit mass or unit volume of the first layer can be determined and the second layer has a homogeneous distribution of a second population of second fluorescent nanoparticle in the second layer wherein the quantity of second fluorescent nanoparticles per unit mass or volume of the second layer can be determined;

(b) irradiating the first layer with a light source of sufficient irradiance to create a population of excited first fluorescent nanoparticle that emits fluorescent light;

(c) measuring the radiance of fluorescent light that is emitted from an area on a surface of the first layer;

(d) irradiating the second layer with a light source of sufficient irradiance to create a population of excited second fluorescent nanoparticle that emits fluorescent light;

(e) measuring the radiance of fluorescent light that is emitted from an area on a surface of the second layer;

(f) calculating a physical property of the first layer based on the measured radiance of fluorescent light that is emitted from the first layer; and (g) calculating a physical property of the second layer based on the measured radiance of fluorescent light that is emitted from the second layer.

In a further aspect, the invention is directed to a method of monitoring the continuous production of a multilayer plastic film, that moves in a machine direction and that is formed by laminating at least two polymeric layers, which method includes the steps of:

(a) forming a first polymer layer comprising a first polymer and a first population of first fluorescent nanoparticle, wherein the quantity of the first fluorescent nanoparticles per unit mass or volume of the first polymeric layer can be determined;

(b) forming a second polymer layer;

(c) forming the multilayer plastic film at a first location wherein the film contains the first polymeric layer and the second polymeric layer;

(d) exposing the first population of first fluorescent nanoparticle to a light source that causes them to emit fluorescent light;

(e) measuring the fluorescent light that is emitted by the first population of first fluorescent nanoparticle at a second location that is downstream from the first location;

(f) calculating the thickness or weight of the first polymeric layer in the multilayer film based on the measured fluorescent light.

DETAILED DESCRIPTION OF PREFERRED EMBODIMENTS

The present invention relates to a process for measuring physical properties of a composition, especially material that is in the form of a multilayer film, web or sheet, by incorporating fluorescent nanoparticles into the composition. While the technique will be illustrated in analyzing multilayer plastic films, it is understood that it can be employed to determine the physical characteristics for a number of different materials including, for example, paper, coated materials, fabrics, and the like.

Fluorescent nanoparticles refer generally to semiconductive particles that exhibit fluorescence when exited by an external excitation source and that have a diameter in the range of about 1 nm to about 1000 nm, preferably in the range of about 5 nm to about 200 nm, more preferably in the range of about 10 nm to about 100 nm. Preferred fluorescent nanoparticles include three-dimensional fluorescent semiconductive nanocrystals or quantum dots which consists of crystalline semiconductors which are small enough so that electrons within suffer from quantum confinement such that the properties of the quantum dots are changed from those of bulk semiconductors. Quantum dots can be manufactured such that their optical emission peaks are very narrow. Different sizes of quantum dots will exhibit different emission spectra yet be all excitable by the same optical source which has an excitation wavelength that is lower than that of the emission peaks. Thus quantum dots of the same material but with different sizes can emit light of different colors. Thus a first population of fluorescent nanoparticles can be formulated to have a different emission peak than a second population of fluorescent nanoparticles when the fluorescent nanoparticles of the first population are either (i) made of different semiconductive material as compared to those of the second population or (ii) made of the same semiconductive materials but have a different selected size distribution as compared to those of the second population.

Figure 1:
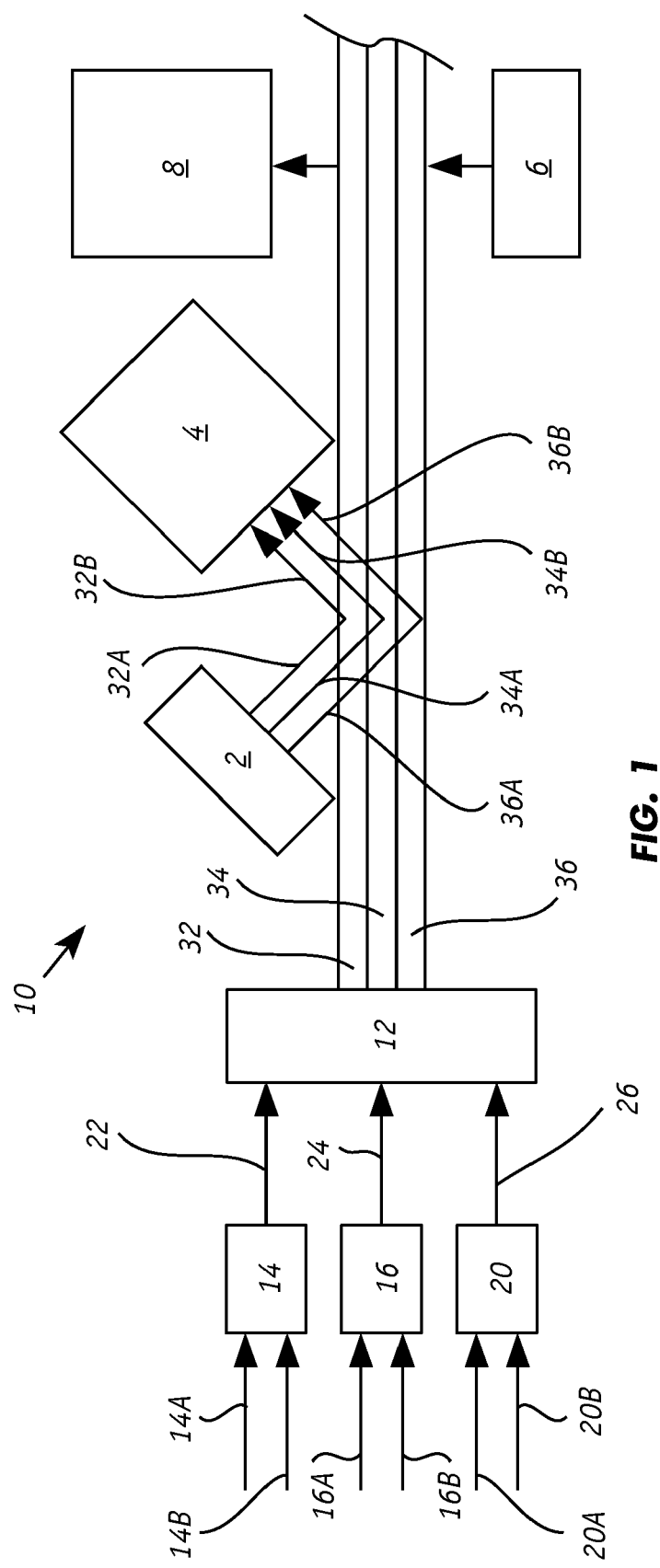
FIG. 1 shows a plastic sheetmaking system implementing the technique of the present invention.

FIG. 1 depicts a system for continuous production of a multilayer film that consists, for illustrative purposes, of three laminated layers 32, 34, and 36. Extruder 12 is connected via lines 22, 24, and 26 to three sources or reservoirs of polymer resin 14, 16 and 20, respectively. For illustrative purposes each layer comprises a different polymer. It is understood that each of the three layers can be made from any polymer or polymer blends and additional operations can occur between extruder 12 and their measurements, for example, the multilayer film can be stretched in one or more directions prior to measurement. Representative extruder machines are further described, for instance, in U.S. Pat. No. 6,793,854 to Kirjavainen, U.S. Pat. No. 6,565,343 to Krycki, U.S. Pat. No. 5,230, 923 to Hirokawa et al., U.S. Pat. No. 4,797,246 to Reinke et al., and U.S. Pat. No. 4,311,658 which are incorporated herein by reference.

Reservoir 14 is connected to a supply of first resin 14A and a supply of first fluorescent nanoparticles 14B. Similarly, reservoir 16 is connected to a supply of second resin 16A and a supply of second fluorescent nanoparticles 16B. Finally, reservoir 20 is connected to a supply of third resin 20A and a supply of third fluorescent nanoparticles 20B. The amounts of resin and fluorescent nanoparticles that are metered into each reservoir are controlled so that their proportions are known. A mixer (not shown) is employed in each reservoir 14, 16, and 20 to thoroughly mix the resins and fluorescent nanoparticles so that the fluorescent nanoparticles are homogeneously distributed within the resin as the individual mixtures enter extruder 12. The result is that, for each layer that is extruded from extruder 12, the number of fluorescent nanoparticles per unit mass is known and the three populations of fluorescent nanoparticles exhibit different emission spectra. Commercially available fluorescent nanoparticles in the form of quantum dots are typically pre-blended (or pre-coated) with polymeric material. The mixing in the reservoir further reduces the concentration of the quantum dots vis-à-vis the polymer material.

Extruder 12 produces a multilayer film consisting of laminated layers 32, 34, and 36 traveling in the machine direction. With the present invention, thickness and other compositional information concerning layers 32, 34, 26 are ascertained by measuring the intensities of the fluorescent lights 32B, 34B and 36B, respectively, which are emitted from the three layers. This measurement is performed with a radiation detector device that includes a source of radiation 2 and a corresponding detector or receiver 4. Radiation 32A, 34A, and 36A from source 2 irradiates layer 32, 34, and 36 respectively, of the multilayer film and receiver 4 measures the radiance of fluorescent lights 32B, 34B, and 36B that are emitted from a known area on the surface the film. As is apparent, if desired, the detector 2 can also be positioned on the opposite side of the film to measure the emissions.

Figure 2:
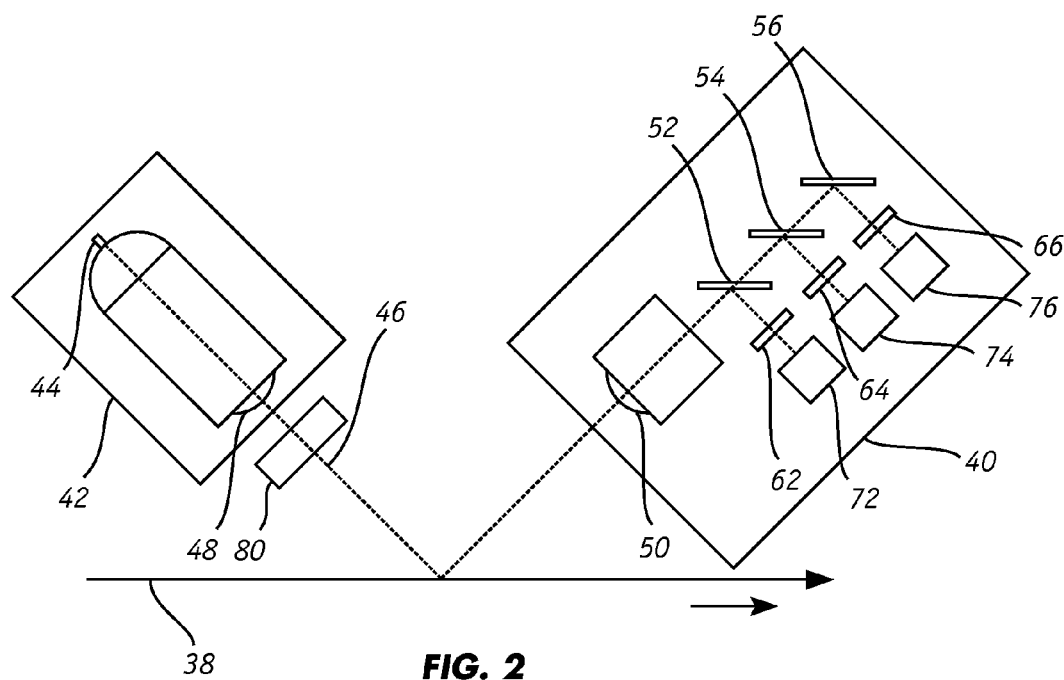
FIG. 2 shows a fluorescent radiation detector assembly.

As shown in FIG. 2, the radiation detector device, which is used to simultaneously measure the thickness of individual layers 32, 34, and 36, includes excitation source 42, such as a tungsten-halogen source 44, of continuous wave radiation in the visible and infrared regions and a detector assembly 40 that includes three infrared detectors that are preferably housed in a temperature-controlled enclosure. Preferably, a high-pass optical filter is positioned in front of source 44 to avoid interference between the light from the excitation source and the fluorescence. The broad-band infrared source energy 44 is directed at multilayer film 38, which consists of laminated layers 32, 34, and 36 (FIG. 1) and detector assembly 40 comprises a sensor for each of the three layers. The layer 32 sensor includes measure filter 62 and detector 72; the layer 34 sensor includes measure filter 64 and detector 74; and the layer 34 sensor includes measure filter 66 and 76. While not critical, the angle between film 38 and detector assembly 40 is preferably about 90 degrees.

Excitation source 42 includes lens 48 which collimate radiation beam 46 to irradiate the surface of multilayer film 38 with sufficient irradiance to excite the fluorescent nanoparticles in each of the three layers. A collimated beam allows the spot on the surface of the film to maintain a constant area even as the sheet of film moves. The intensity of radiation beam 46 is measured by a photometer 80, which can include a beam splitter and detector assembly. Another technique of measuring the intensity of radiation beam 46 is to meter the light intensity near the tungsten-halogen reflector by drilling pinholes therein. Still another method is to periodically insert a fluorescent tile between source 2 and detector 4 (FIG. 1). In order to obtain consistent measurements even if the correlation between the intensity of the excitation source and the intensity of the fluorescence emission is non-linear, excitation source 42 can be controlled to maintain radiation beam 46 at the same intensity levels. Alternatively, the intensity of beam 46 can be adjusted to create a saturated population of excited fluorescent nanoparticles.

Suitable optics including collection lens 50 captures the radiance of radiation that is emitted by decaying fluorescent nanoparticles from a known area on the surface of multilayer film 38. It should be noted that it is not necessary to know the surface area on of multiyear film 38 from which radiance is captured in order to employ this technique to measure thickness and other physical characteristics of the individual layers containing the fluorescent nanoparticles. Rather, when the surface area is not known, it is critical that this surface area be fixed or unchanging during measurement, with respect to each layer, since the sensor can be calibrated without having measured the actual surface area. In principle, a different known or fixed surface area can be employed when measuring the radiance from different layers of the multilayer film; however, in practice it is easier to use the same known or fixed surface area for each layer.

The energy emitted from the area on multilayer film 38 is analyzed by passing beam 46 through beam splitters or dichroic mirrors 52, 54, and 56 and filters 62, 64, and 66, respectively, and onto the individual detectors. Detector 72, 74 and 76 measures the amount of radiation emitted by the fluorescent nanoparticles from layers 32, 34, and 36, respectively. The detectors can comprise, for example, a photomultiplier tube, avalanche photodiodes or electron multiplying charge-coupled device. This configuration of the optical analyzer comprising the beam splitters, filters, and detectors insures that all detector signals originate simultaneously from the same area of multilayer film 38. Alternatively, a single sensor with multiplexed configuration can be employed to detect the signals simultaneously. As another alternative, an array of detectors and a continuously variable filter or a grating or prism type spectrometer (with a single detector or array of detectors) can be used.

Excitation source 42 and detector assembly 40 can be designed to scan back and forth along a cross direction which is perpendicular to the machine direction (MD) of the moving film. In this fashion, thickness information of the film in both machine direction and cross direction (CD) is ascertained. Scanning mechanisms for synchronized movement are described, for example, in U.S. Pat. No. 5,094,535 to Dahlquist et al., U.S. Pat. No. 4,879,471 to Dahlquist, U.S. Pat. No. 5,315,124 to Goss et al, and U.S. Pat. No. 5,432,353 to Goss et al., which are incorporated herein by reference.

In operation, as shown in FIG. 1, the thickness of each of the three layers 32, 34, and 36 in the multilayer film formed by extruder 12 can be continuously monitored as the film travels downstream between radiation source 2 and detector 4. The CD and MD measurements generated by the process can be employed to control the sheetmaking process in order to produce multilayer films with the desired individual layer thicknesses. Alternatively, the system can be employed periodically to precisely monitor the thicknesses during critical periods such as during initial startup. In this fashion, the fluorescent nanoparticles are employed only when needed. During normal or non-critical periods of operations, the thickness can be monitored by conventional thickness and/or basis weight measuring apparatus that include non-contact optical sensors 8, 6. Conventional instruments and techniques for these procedures are described, for example, in U.S. Pat. No. 4,767,935 to Anderson et al, U.S. Pat. No. 4,879,471 to Dahlquist and U.S. Pat. No. 6,281,679 to King et al., which are incorporated herein by reference. As is apparent, measurements from the inventive technique can be employed to calibrate these conventional instruments.

In the case where only a single layer of plastic film or only a single layer within a multilayer film is to be monitored, an appropriate amount of any suitable fluorescent nanoparticle can be employed to formulate the resin/fluorescent nanoparticle mixture for the single layer. However, for the case of the three layer composition being analyzed in FIG. 1, three different populations of fluorescent nanoparticles, which emit fluorescent light at different wavelengths, are needed. In other words, each population of fluorescent nanoparticles exhibits an emission spectrum that is different from those of the other populations used in the same application. Preferably, the different populations of fluorescent nanoparticles are excited by the same optical source which emits light that has a wavelength that is shorter than that of the measured radiation. Alternatively, the different populations can be excited by radiation having different wavelengths.

The thickness of any particular layer in the multilayer film can be calculated by applying the relationship that its thickness $t=k \times L/(N \times d)/I$, where k is a proportionality constant that is specific to the particular layer, L is the radiance of measured optical emission from the decaying fluorescent nanoparticles per unit area at the particular layer, N is the number of fluorescent nanoparticles per unit mass of the layer, d is the density of the layer and I is the incident light at the particular layer. Both I and L can suffer from attenuation by other layers present in the structure. The amount of attenuation can be calculated using known attenuation factors or factors obtained by calibration. It should be noted that when excitation source 44 is not controlled to either maintain beam 46 at constant intensity or establish a saturated population of excited fluorescent nanoparticles, then it is preferred, for the above thickness calculation, that the radiance L be normalized by the measured intensity of beam 46 (FIG. 1). The proportionality constant k can be determined by calibration with a standard of known thickness created with known mass and known number of fluorescent nanoparticles per unit mass. The density of a layer of plastic film can be measured conventionally by ultrasound or a die, weigh and caliper method. Once the thickness of a layer is calculated, its basis weight, which is expressed as mass per unit area, can be readily calculated.

As is apparent, in order to determine a physical property of a layer, it is not necessary to know the amount of fluorescent nanoparticles per unit mass or volume that is present in the layer of interest, as a calibration can be performed without knowing the actual amount. For example, a plastic layer can be prepared by homogenously mixing a small known amount (e.g., a few grams) of nanoparticles per ton of plastic resin. Once the plastic layer, incorporating the fluorescent nanoparticles, is fabricated the fluorescence intensity from a layer sample is measured and correlated with the sample's measured thickness in the laboratory. Thus, while the quantity of fluorescent nanoparticles per unit mass or volume can be determined, e.g., calculated, it is not necessary to do so.

Suitable quantum dots are available from Evident Technologies (Troy, N.Y.) and are marketed as (i) EVITAGS which are quantum dots that are integrated into resins and polymer matrix materials. The latter type of quantum dots can be employed in plastics applications. The quantum dots have a core of CdSe and a ZnS shell. For infrared applications they have InGaP core and a ZnS shell; and (ii) EVIDOTS which are quantum dots that have tunable optical and electronic properties imparted from particle composition and size. For papermaking and other aqueous applications, water-stable quantum dots are preferred. Quantum dots can be embedded in various types of plastics including polycarbonates, polystyrene, polymethyl methacrylate, and polyethylene and commercially available, for instance, from Evident Technologies. Preferred quantum dots emit near infrared fluorescence upon exposure to visible or ultraviolet light illumination. Suitable quantum dots must be robust enough to withstand industrial processes where they are applied.

The amount of fluorescent nanoparticles employed should be limited so as not to adversely affect the structural integrity of the layers to which they are added. Typically, incorporating two million particles per square meter for each species of fluorescent nanoparticle is sufficient. When the layer of material is newsprint paper, this is equivalent to approximately one picogram/kg of newsprint or $10^{-14}$ g/m². In a related aspect, it is expected that when the concentration of fluorescent nanoparticles within a layer is very high, the proportionality between absorbance of irradiating radiation and (i) the known number of fluorescent nanoparticles per unit mass of the layer and (ii) the distance traversed within the fluorescent nanoparticles containing layer by the irradiating radiation can become non-linear. Thus, in many applications it is preferred to distribute a homogeneous distribution of the fluorescent nanoparticles of narrow size into a layer of material of interest at a known number of fluorescent nanoparticles per mass of the material such that the concentration of fluorescent nanoparticles is sufficiently small to maintain direct linear proportionality.

Another application of the invention is to measure the thickness of paper products and particularly of multiply paper. Paper is manufactured on continuous papermaking machines whereby a web of paper is formed from an aqueous suspension of fibers (stock) on a traveling mesh wire or fabric and water drains by gravity and vacuum suction through the fabric. The web is then transferred to a pressing section where more water is removed by dry felt and pressure. The web next enters the dryer section where steam heated dryers and hot air completes the drying process. The papermaking machine is essentially a de-watering system. Multiply products are produced by consolidating two or more web plies into a single sheet.

By incorporating fluorescent nanoparticles into the stock so that the proportion of fluorescent nanoparticles, fiber, and other paper components, such as ash, are known, the thicknesses of the individual layers of paper in a multiply product can be monitored in the same fashion as for the multilayer plastic described above. However, in manufacturing of paper, some fluorescent nanoparticles will be drained from the wet stock. To reduce the level of drainage, fluorescent nanoparticles can be attached to the components in the stock. For example, bifunctional surface modifiers can be used to link quantum dots to ash particle ($TiO_2$) surfaces. See "Assembly of CdS quantum dots onto mesoscopic TiO2 films for quantum dot-sensitized solar cell applications," Yu-Jen Shen and Yuh-Lang Lee, 2008 Nanotechnology (19) 045602. Different species of quantum dots can thus be attached to corresponding ash particles. Surface-modified quantum dots that are water stable are described in U.S. Pat. No. 7,192,780 to Liu et al., U.S. Pat. No. 6,872,450 to Liu et al, and U.S. Pat. No. 6,649,138 to Adams et al., which are all incorporated herein by reference.

In addition, polymeric retention aids are employed to papermaking to improve the retention of fines at the wire. US Patent Application 2007/0258316 to Matula describes improved methods of introducing polymeric retention aids into the paper making process whereby the polymeric structure of the retention aid remains intact. US Patent Application 2007/0119561 to Doelle et al. describe a method of loading cellulose fibers with calcium carbonate; the so-treated fibers are capable of retaining much higher levels of ash. Thus, another technique of incorporating fluorescent nanoparticles to components of the wet stock is to first attach quantum dots to polymeric retention aids. It is believed that these modified polymers will adhere to treated and non-treated cellulose fibers.

Fluorescent nanoparticles can also be attached to cellulose fibers to yield tagged-fibers. An advantage of being attached to fibers is that the fluorescent nanoparticles are less likely to be removed in the de-watering process. Attachment can be accomplished through covalent bonding, adsorption, and physical immobilization. Quantum dots can also be encapsulated with polymers with specific physical properties as described in U.S. Pat. No. 7,081,489 to Chen et al., which is incorporated herein by reference. For paper applications, suitable polymers are preferably water insoluble, thermoplastics which include, but are not limited to, polyamides, polycarbonates, polyalkenes, polyvinyl ethers, polyglycolides, cellulose ethers, (e.g., hydroxy propyl cellulose, hydroxy propyl methyl cellulose, and hydroxy butyl cellulose), polyvinyl halides, polyglycolic acid, and polylactic acid.

Figure 3:
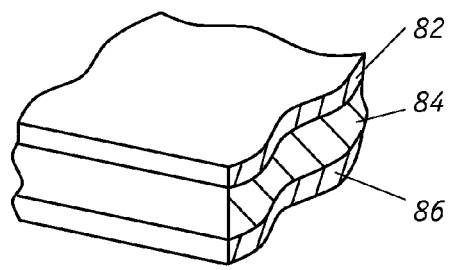
FIG. 3 is a cross-sectional view of a coated sheet.

A further embodiment of the inventive process provides on-line measurements of one or more components in coated paper. Techniques for coating paper sheets are described in U.S. Pat. No. 7,255,918 to Watanabe et al. and U.S. Pat. No. 6,074,483 to Belotserkovsky et al., which are incorporated herein by reference. FIG. 3 shows base sheet 84 that has an upper coating 82 and lower coating 86. The thickness for any or all three layers can be measured by incorporating appropriate species of fluorescent nanoparticles and detecting their emission spectra.

For example, in the production of high gloss paper, a thin coating 82 containing $CaCO_3$ is applied to the base sheet 84. The invention provides an on-line non-contact method of simultaneously measuring the thickness of the gloss coating and that of the base sheet. In particular, when wet stock is formulated, a predetermined amount of a first population of fluorescent nanoparticles also is incorporated. Thus, the base sheet paper that is made will have the nanoparticles homogeneously incorporated therein. Similarly, when the gloss formulation is prepared with a known amount of $CaCO_3$ and other materials, a predetermined amount of a second population of fluorescent nanoparticle is also added. Preferably, both populations of fluorescent nanoparticles are excited by the same optical source which generates radiation with a narrow wavelength band, and the first species emits radiation having a longer wavelength than that emitted by the second species. As the homogeneously mixed gloss coating is applied onto the base sheet, a scanning source and detector located downstream travel back-and-forth cross the traveling paper to measure the intensities of the fluorescent light that are emitted by the first and second species. In this fashion, both cross direction and machine direction individual thickness profiles of the base paper and coating can be generated.

As is apparent, the inventive technique is most suited when the radiation emitted from the fluorescent nanoparticles is readily transmitted through the material into which the fluorescent nanoparticles are incorporated. In the case where fluorescent nanoparticles are part of in a thin optically transparent layer that is an outer layer in the multilayer film, the transmission losses are small and essentially all of the radiation can be detected. However, in the case where the fluorescent nanoparticles are incorporated into an interior layer of a multilayer structure, then attenuation of the emitted radiation due to absorption and scattering is likely and this phenomenon must be accounted for. One method of compensating for this is to recognize that longer wavelength radiation scatter less and thus travel farther than shorter wavelength radiation, thus, fluorescent nanoparticles that emit radiation with longer wavelengths should be used in the interior layers. In a similar vein, the excitation light will be absorbed and scattered by the material in which the fluorescent nanoparticles are incorporated. The wavelength of the excitation radiation is preferably selected to minimize absorption and the intensity of the excitation radiation is adjusted in accordance with the thickness of the material.

The foregoing has described the principles, preferred embodiments and modes of operation of the present invention. However, the invention should not be construed as being limited to the particular embodiments discussed. Thus, the above-described embodiments should considered as illustrative rather than restrictive, and it should be appreciated that variations may be made in those embodiments by workers skilled in the art without departing from the scope of the present invention as defined by the following claims.

What is claimed is:

1. A method or non-contact determination of a physical property of a layer of composition that comprises the steps of:
   (a) introducing a homogeneous distribution of a single population of fluorescent nanoparticles into the layer wherein the quantity of fluorescent nanoparticles per unit mass or volume of the layer can be determined;
   (b) irradiating the layer with a light source of sufficient irradiance to create a population of excited fluorescent nanoparticles that emit fluorescent light;
   (c) measuring the radiance of fluorescent light that is emitted from an area on a surface of the layer; and
   (d) calculating the physical property based on the measured radiance of the fluorescent light.

2. The method of claim 1 wherein step (d) calculates the thickness or basis weight of the layer.

3. The method of claim 2 wherein step (d) comprises calculating the thickness of the layer by using the direct proportionality between the measured radiance of the fluorescent light emission from the fluorescent nanoparticles per unit area and quantity of fluorescent nanoparticles per unit mass or per unit volume in the layer.

4. The method of claim 1 wherein the layer of composition is one layer of a multilayer structure.

5. The method of claim 1 wherein step (c) comprises measuring the radiance of fluorescent light that is emitted from a known or fixed area on the surface of the layer.

6. The method of claim 1 wherein step (a) comprises forming an initial web of composition that travels along in a machine direction and step (c) comprises obtaining radiation measurements at multiple locations in the machine direction, in a cross direction, or in both directions wherein radiation measurements that are obtained at the multiple locations measures the radiance of fluorescent light that is emitted from a known or fixed area on a surface of the layer.

7. The method of claim 1 wherein step (b) comprises exposing the layer to radiation including wavelengths in at least a first wavelength regions and step (c) comprises measuring radiation that is emitted by the fluorescent nanoparticles having wavelengths at a second wavelength region.

8. A method of measuring a physical property of at least two individual layers in a multilayer structure that comprises the steps of:

(a) forming a multilayer structure that has at least two layers including a first layer and a second layer wherein the first layer has a homogeneous distribution of a single population of first fluorescent nanoparticles in the first layer wherein the quantity of first fluorescent nanoparticles per unit mass or unit volume of the first layer can be determined and the second layer has a homogeneous distribution of single population of second fluorescent nanoparticles in the second layer wherein the quantity of second fluorescent nanoparticles per unit mass or unit volume of the second layer can be determined;

(b) irradiating the first layer to a light source of sufficient irradiance to create a population of excited first fluorescent nanoparticles that emit fluorescent light;

(c) measuring the radiance of fluorescent light that is emitted from an area on a surface of the first layer;

(d) irradiating the second layer to a light source of sufficient irradiance to create a population of excited second fluorescent nanoparticles that emit fluorescent light;

(e) measuring the radiance of fluorescent light that is emitted from an area on a surface of the second layer;

(f) calculating a physical property of the first layer based on the measured radiance of fluorescent light that is emitted from the first layer; and (g) calculating a physical property of the second layer based on the measured radiance of fluorescent light that is emitted from the second layer.

9. The method of claim 8 wherein step (f) calculates the thickness of the first layer and step (g) calculates the thickness of the second layer.

10. The method of claim 9 wherein each of steps (f) and (g) comprises calculating the thickness of the layer by using the direct proportionality between the measured radiance of the fluorescent light emission from the fluorescent nanoparticles per unit area and quantity of fluorescent nanoparticles per unit mass or volume in the layer.

11. The method of claim 8 wherein the multilayer structure comprises a multilayer plastic film.

12. The method of claim 8 wherein step (b) comprises exposing the first layer to radiation including wavelengths in at least a first wavelength region, step (c) comprises measuring radiation that is emitted by the fluorescent nanoparticles having wavelengths at a second wavelength region, and step (d) comprises exposing the second layer to radiation including wavelengths in at least the first wavelength region, and step (e) comprises measuring radiation that is emitted by the fluorescent nanoparticles having wavelengths at a third wavelength region.

13. A method of monitoring the continuous production of a multilayer plastic film, that moves in a machine direction and that is formed by laminating at least two polymeric layers, which method comprises the steps of:

(a) forming a first polymer layer comprising a first polymer and a single population of first fluorescent nanoparticles, wherein the quantity of the first fluorescent nanoparticles per unit mass or volume of the first polymeric layer can be determined;

(b) forming a second polymer layer;

(c) forming the multilayer plastic film at a first location wherein the film contains the first polymeric layer and the second polymeric layer;

(d) exposing the population of first fluorescent nanoparticles to a light source that causes them to emit fluorescent light;

(e) measuring the fluorescent light that is emitted by the population of first fluorescent nanoparticles at a second location that is downstream from the first location; and (f) calculating the thickness or weight of the first polymeric layer in the multilayer film based on the measured fluorescent light.

14. The method of claim 13 further comprising step (g) of controlling the thickness of the first polymer layer that is formed in step (a) in response to thickness calculations made in step (f).

15. The method of claim 13 where in step (a) comprises forming a second polymer layer comprising a second polymer and a single population of a second fluorescent nanoparticles, wherein the quantity of the second fluorescent nanoparticles per unit mass or unit volume of the second polymeric layer can be determined, and further comprising the steps of:

(g) exposing the population of second fluorescent nanoparticles to a light source that causes them to emit fluorescent light;

(h) measuring the fluorescent light that is emitted by the second fluorescent nanoparticles at a second location that is downstream from the first location;

(i) calculating the thickness of the second polymeric layer in the multilayer film based on the measured fluorescent light.

16. The method of claim 15 wherein the first polymer is different from the second polymer.

17. The method of claim 15 wherein the population of first fluorescent nanoparticles and the population of second fluorescent nanoparticles are exposed to a broadband source of radiation.

18. The method of claim 13 further comprising step (g) of using the calculated thickness or weight in step (f) to calibrate a thickness or weight measuring device.

19. The method of claim 13 wherein the step (e) comprises obtaining radiation measurements at multiple locations in the machine direction, in a cross direction, or in both directions.

20. A method of measuring a physical property of at least two individual layers in a multilayer structure that comprises the steps of:

(a) forming a multilayer structure that has at least two layers including a first layer and a second layer wherein the first layer has a homogeneous distribution of a first population of first fluorescent nanoparticles in the first layer wherein the quantity of first fluorescent nanoparticles per unit mass or unit volume of the first layer can be determined and the second layer has a homogeneous distribution of second population of second fluorescent nanoparticles in the second layer wherein the quantity of second fluorescent nanoparticles per unit mass or unit volume of the second layer can be determined;

(b) irradiating the first layer to a light source of sufficient irradiance to create a population of excited first fluorescent nanoparticles that emit fluorescent light by exposing the first layer to radiation including wavelengths in at least a first wavelength region;

(c) measuring the radiance of fluorescent light that is emitted from an area on a surface of the first layer by measuring radiation that is emitted by the fluorescent nanoparticles having wavelengths at a second wavelength region;

(d) irradiating the second layer to a light source of sufficient irradiance to create a population of excited second fluorescent nanoparticles that emit fluorescent light by exposing the second layer to radiation including wavelengths in at least the first wavelength region;

(e) measuring the radiance of fluorescent light that is emitted from an area on a surface of the second layer by measuring radiation that is emitted by the fluorescent nanoparticles having wavelengths at a third wavelength region;

(f) calculating a physical property of the first layer based on the measured radiance of fluorescent light that is emitted from the first layer; and (g) calculating a physical property of the second layer based on the measured radiance of fluorescent light that is emitted from the second layer.

21. A method of monitoring the continuous production of a multilayer plastic film, that moves in a machine direction and that is formed by laminating at least two polymeric layers, which method comprises the steps of:

(a) forming a first polymer layer comprising a first polymer and a first population of first florescent nanoparticles, wherein the quantity of the first fluorescent nanoparticles per unit mass or volume of the first polymeric layer can be determined;

(b) forming a second polymer layer;

(c) forming the multilayer plastic film at a first location wherein the film contains the first polymeric layer and the second polymeric layer;

(d) exposing the first population of fluorescent nanoparticles to a light source that causes them to emit fluorescent light;

(e) measuring the fluorescent light that is emitted by the population of first fluorescent nanoparticles at a second location that is downstream from the first location;

(f) calculating the thickness or weight of the first polymeric layer in the multilayer film based on the measured fluorescent light; and (g) using the calculated thickness or weight in step (f) to calibrate a thickness or weight measuring device.

* * * * *